US012728091B2

(12) United States Patent
Rees

(10) Patent No.: US 12,728,091 B2
(45) **Date of Patent: *Sep. 8, 2026**

(54) INTRAORAL CLEANING TABLET

(71) Applicant: Frank Rees, Tweed Heads (AU)

(72) Inventor: Frank Rees, Tweed Heads (AU)

( * ) Notice: Subject to any disclaimer, the term of this patent is extended or adjusted under 35 U.S.C. 154(b) by 0 days.

This patent is subject to a terminal disclaimer.

(21) Appl. No.: 19/561,262

(22) Filed: Mar. 9, 2026

(65) Prior Publication Data

US 2026/0224471 A1 Aug. 6, 2026

Related U.S. Application Data

(63) Continuation-in-part of application No. 19/339,250, filed on Sep. 24, 2025, now Pat. No. 12,594,235, and a continuation-in-part of application No. 18/072,437, filed on Nov. 30, 2022, now abandoned.

(51) Int. Cl.

| | |
|---|---|
| ***A61K 8/9789*** | (2017.01) |
| ***A23G 4/06*** | (2006.01) |
| ***A23G 4/08*** | (2006.01) |
| ***A23G 4/10*** | (2006.01) |
| ***A61K 8/02*** | (2006.01) |
| ***A61K 8/34*** | (2006.01) |
| ***A61K 8/73*** | (2006.01) |
| ***A61Q 11/00*** | (2006.01) |

(52) U.S. Cl.

CPC ............ *A61K 8/9789* (2017.08); *A23G 4/068* (2013.01); *A23G 4/08* (2013.01); *A23G 4/10* (2013.01); *A61K 8/0204* (2013.01); *A61K 8/345* (2013.01); *A61K 8/732* (2013.01); *A61Q 11/00* (2013.01); *A61K 2800/92* (2013.01)

(58) Field of Classification Search

CPC ........ A61K 8/9789; A61K 8/345; A61K 8/73; A61K 8/922; A61K 2800/92; A61Q 11/00

See application file for complete search history.

(56) References Cited

U.S. PATENT DOCUMENTS 2,812,256 A * 11/1957 Nerfin .................. A61K 9/0058 424/48

2006/0078509 A1 * 4/2006 Gebreselassie ......... A23P 30/10 426/660

FOREIGN PATENT DOCUMENTS

| | | | | |
|---|---|---|---|---|
| CN | 109105790 A * | 1/2019 | ............. | A23L 33/00 |
| DE | 102011084162 A1 * | 4/2013 | ............. | A23L 27/12 |
| WO | WO-2024003682 A1 * | 1/2024 | ............... | A23G 4/10 |

* cited by examiner

*Primary Examiner* — Lezah Roberts

(74) *Attorney, Agent, or Firm* — Daniel Polk

(57) ABSTRACT

An intraoral cleaning composition is provided in the form of a chewable gum or tablet that can remove plaque and debris from teeth, gums, and oral surfaces without requiring water or brushing. The composition includes a chewable gum base configured to stimulate saliva and a fibrous ingestible material embedded within the gum matrix to provide mechanical cleaning during mastication. In certain embodiments, the fibrous material comprises freeze-dried apple peel and fermented dried apple peel. The composition may further include a dietary fiber system comprising resistant starch and soluble acacia-derived fiber. Sweetening agents such as erythritol may be included to provide palatability while avoiding added sugars. Additional ingredients may include waxes, flavoring agents, antioxidants, and mineral additives. The composition is plastic-free and biodegradable and may be safely ingested after chewing while providing oral hygiene benefits through combined mechanical and biochemical cleaning action.

20 Claims, No Drawings

INTRAORAL CLEANING TABLET

CROSS-REFERENCE TO RELATED APPLICATION

This application is a continuation in part of U.S. patent application Ser. No. 18/072,437, filed on Nov. 30, 2022 and U.S. patent application Ser. No. 19/339,250 filed on Sep. 24, 2025, which are hereby incorporated by reference in its entirety.

FIELD OF DISCLOSURE

The present invention relates to the dental industry and, more particularly to an intraoral cleaning tablet which is safe to ingest, and which can remove plaque and debris from the teeth, gums and the oral cavity without the use of water.

BACKGROUND

The most common way to clean teeth is with a toothbrush and toothpaste; however, it is not always convenient to use these items, and running water for rinsing the mouth may not always be available. Certain alternative oral care products exist, such as oral care strips produced by Pfizer Inc. and sold under the Listerine trademark, which dissolve in the mouth and freshen breath, but such strips do not effectively clean the teeth. Chewable toothpaste tablets are also known and can form toothpaste in the mouth when mixed with saliva; however, a toothbrush is still required to remove debris and plaque, and many such tablets are not intended to be safely ingested, making them impractical when water is unavailable for rinsing. Traditional chewing gums may freshen the mouth, but they generally are not ingestible, or are not recommended for ingestion, because most chewing gums contain plastic-based gum bases that are indigestible. Accordingly, there remains a need for an oral hygiene product that is safe to ingest and capable of removing plaque and debris from the teeth, gums, and oral cavity without the use of water.

SUMMARY

According to the present disclosure, there is provided an intraoral cleaning tablet comprising:

(a) a chewable gum configured to stimulate saliva; and (b) a fibrous ingestible material, wherein:

(i) the fibrous ingestible material comprises dried apple peel embedded within the chewable gum and configured to mechanically clean the teeth; and (ii) the chewable gum is plastic-free and biodegradable.

The term ‘tablet’ can include any substance to be put into the mouth, including gums, jubes or cubes of any shape. The tablets may be coated or uncoated.

The chewable gum may include mastic gum (pistacia lentiscus), chicle, gum Arabic, gum acacia, Chios Mastic Tree gum resin, glycerol, or waxes (such as bee’s wax, carnauba wax, Candelilla wax).

The tablet may include a lubricant, such as magnesium stearate (produced from palm oil), or a combination of other ingredients such as rice extract, rice hulls, gum arabic and sunflower oil.

Preferably, the fibrous material is freeze-dried before being embedded within the chewable gum. The fibrous material may be compressed and freeze-dried.

The chewable gum may contain additives, such as calcium including calcium phosphate (mono basic, dibasic or tribasic), calcium glycero-phosphate, calcium citrate, calcium carbonate, calcium lactate. The chewable gum may contain other additives such as sodium bicarbonate, commiphora myrrha (myrrh) gum oleoresin powder, piper nigrum (black pepper) essential oil, or Xylitol.

Preferably, the tablet also contains a gelatinous substance, such as agar. The gelatinous substance may contain agents for polishing, flavouring, breath freshening and/or desensitising the teeth. The gelatinous substance may also include a health supplement, such as zinc or fluoride. The gelatinous substance may include catalytic nanozyme to reduce plaque.

The breath freshening agent may be one or more essential oils, such as mint, spearmint, peppermint, eucalyptus, piper nigrum (black pepper) oil, citrus oils (such as lemon or orange), cloves, cinnamon, or ginger.

The tablet may include menthol as a cooling and flavouring agent.

According to another aspect of the present invention, there is provided a method of making an intraoral cleaning tablet comprising the steps of:

(a) collecting apple peel;

(b)drying the apple peel;

(c) blending the apple peel with other ingredients for the tablet to form a composition;

(d) compressing the composition; and (e) forming the composition into a tablet.

The method may also include a step of coating the tablet in a gum. The method may also include the step of freezing the dried apple peel.

Preferably, the fibrous ingestible material is organic and contains no pesticides or herbicides.

Any of the features described herein can be combined in any combination with any one or more of the other features described herein within the scope of the invention.

DETAILED DESCRIPTION

The fibrous ingestible material in the form of apple peel, which is embedded within a chewable gum. The gum is preferably mastic gum but may also be chicle.

The tablet could be in the form of a hard tablet, or soft gum or jube.

The tablet can be coated or uncoated.

When the tablet is chewed, the apple peel removes the plaque and debris from the teeth, gums and oral cavity.

The apple peel is an organic material which is inherently flavoured. If the apple peel is swallowed, it would do no harm.

Chewing or sucking the tablet can help to remove plaque and stimulate saliva.

The tablet is moved around within the mouth by the tongue, cheeks and lips to clean all areas of the mouth and teeth.

The tablet contains additives, such as essential oils (including eucalyptus oil or peppermint oil). Peppermint oil is a popular essential oil used alone and in combination with other essential oils. Menthol is the main component of peppermint oil and is responsible for the noticeable cooling sensation.

The tablet may include health supplements, such as zinc, fluoride, and Vitamin C, prebiotics, probiotics, postbiotics and herbal ingredients.

The tablet may also include catalytic nanozyme to reduce plaque.

The intraoral cleaning tablet is made by:

(a) collecting apple peel;

(b) drying the apple peel;

(c) blending the apple peel with other ingredients for the tablet to form a composition;

(d) compressing the composition; and (e) forming the composition into a tablet.

The method preferably includes the step of freezing the dried apple peel. The method may include a step of coating the tablet in a gum.

The present invention provides an oral hygiene product which is safe to ingest because it contains organic ingredients that are plastic-free and biodegradable, which can remove plaque and debris from the teeth, gums and the oral cavity without the use of water.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

In certain embodiments, the chewing gum composition comprises about 40-55% chicle gum base, 25-35% erythritol, 2-6% freeze dried apple peel, 2-6% fibre gum B, 2-6% fermented dried apple peel, 2-5% carnauba wax, 1-4% acetylated distarch adipate, 1-4% novelose resistant starch, 0.5-2% calcium carbonate, 0.5-2% magnesium stearate, 0.5-2% peppermint oil, 0.5-2% natural apple flavour, 0.1-1% natural peppermint flavour, 0.1-1% glycerol, 0.05-0.5% stevia, 0.01-0.2% vitamin E, and optionally up to 0.1% thaumatin and/or up to 0.1% citric acid.

In certain embodiments, the chewing gum composition described herein may be enclosed within an edible, prebiotic wrapper. The wrapper may take the form of a thin film, a sheet that fully wraps the gum, or a pouch or envelope that surrounds the gum piece in an air-tight manner. In another embodiment, the wrapper may form a pouch around the gum in a bag-like configuration, which may be either airtight or non-airtight, depending on the desired storage and functional properties. The wrapper not only serves as packaging but also provides an additional functional benefit by delivering prebiotic dietary fibers that support gut health. Suitable prebiotic materials for forming the edible wrapper include, but are not limited to, pullulan, inulin, fructooligosaccharides (FOS), galactooligosaccharides (GOS), resistant starch, pectin, arabinoxylans, beta-glucans, and gum arabic. These materials may be combined with edible film-forming agents such as hydroxypropyl methylcellulose (HPMC), methylcellulose, starch derivatives, or alginate to achieve desirable mechanical strength, flexibility, and dissolution properties.

The wrapper may be prepared as a thin film using solvent casting, extrusion, or compression molding techniques, and may optionally incorporate plasticizers (e.g., glycerol, sorbitol, or maltitol) to improve flexibility. Flavoring agents (such as natural fruit extracts, essential oils, or sweeteners like stevia) and colorants (such as plant-based pigments) may also be included to enhance palatability and consumer appeal. In some embodiments, the wrapper is designed to dissolve rapidly in the oral cavity, releasing prebiotic fibers concurrently with mastication of the gum.

In one embodiment, the chewing gum composition is enclosed in an edible, prebiotic wrapper formulated from approximately 40% w/w inulin, 40% w/w pullulan, 15% w/w glycerol, 3% w/w natural apple extract, and 2% w/w stevia. The inulin and pullulan are dissolved in deionized water at 60° C. with continuous stirring until a homogeneous solution is achieved. Glycerol is then added as a plasticizer to impart flexibility to the film, after which natural apple extract and stevia are incorporated as flavoring and sweetening agents. The solution is cast onto a sterile, flat glass or stainless steel surface to form a uniform layer approximately 0.2 mm thick. The film is dried at 40° C. under controlled humidity (30-40% RH) for 12 hours until the moisture content is below 10%. Once dried, the film is cut into rectangular sheets sized appropriately to wrap individual gum pieces. The resulting wrapper is flexible, transparent, and capable of tightly enclosing the gum without tearing. Upon oral dissolution, the wrapper releases inulin as a prebiotic fiber, along with flavor and sweetness, thereby enhancing the functional and sensory profile of the gum product.

Additional Embodiments

In certain embodiments, the intraoral cleaning tablet comprises a structured chewing gum composition formulated as a plastic free and biodegradable gum matrix incorporating both mechanical and biochemical cleaning components.

In some embodiments the chewing gum comprises a chicle gum base, the chicle gum base may comprise at least 35 percent by weight of the total chewing gum composition, and in certain embodiments comprises from about 40 percent to about 55 percent by weight of the total composition. The relatively high chicle gum base loading provides chew resilience and structural integrity during mastication while enabling embedding of fibrous and starch components.

In some embodiments the chewing gum has a polyol sweetener such as erythritol. Erythritol may comprise at least 20 percent by weight of the total chewing gum composition, and in certain embodiments comprises from about 25 percent to about 40 percent by weight of the total composition.

In some embodiments the chewing gum has fibrous components such as freeze-dried apple peel and fermented dried apple peel. In some embodiments the freeze-dried apple peel and fermented dried apple peel are present in substantially equal amounts. Substantially equal amounts may include weight ratios ranging from 40:60 to 60:40 relative to one another. In certain embodiments, the combined freeze-dried and fermented apple peel comprises from about 3 percent to about 16 percent by weight of the total composition.

The chewing gum composition further comprises a dietary fiber system including (i) a resistant starch and (ii) a soluble acacia derived fiber. The resistant starch is distinct from fiber naturally present in the apple peel components. As used herein, "distinct" means that the resistant starch is separately added as a purified or modified starch ingredient and is not merely the intrinsic insoluble fiber of the apple peel.

The resistant starch may comprise one or more resistant starch types, including type 2 resistant starch (native granular starch resistant to digestion) and/or type 4 resistant starch (chemically modified starch). In certain embodiments, the resistant starch comprises high-amylose maize starch and/or a chemically modified distarch such as acetylated distarch adipate or other cross-linked starch derivatives. In certain embodiments, the total resistant starch content comprises from about 1 percent to about 10 percent by weight of the total composition. In more particular embodiments, the total resistant starch content comprises from about 1 percent to about 5 percent by weight of the total composition. In certain embodiments, acetylated distarch adipate may additionally function as a texturizing and stabilizing agent.

The soluble acacia derived fiber comprises gum arabic (also known as gum acacia) obtained from the exudate of Acacia species, including Acacia senegal and Acacia seyal. The acacia derived fiber may comprise a high soluble dietary fiber content, such as at least about 70 percent, and in certain embodiments at least about 80 percent, soluble dietary fiber by weight on a dry basis. In certain embodiments, the soluble acacia derived fiber is present in an amount from about 2 percent to about 6 percent by weight of the total composition.

In certain embodiments, the soluble acacia derived fiber comprises commercially available products sold under trade designations such as "Fibre Gum B," provided that such products comprise acacia gum-based soluble dietary fiber as described herein. The term encompasses functionally equivalent acacia gum-based soluble fiber ingredients and is not limited to any particular supplier, proprietary formulation, or geographic market. The acacia derived fiber may improve texture, reduce erythritol crystallization, and contribute to structural cohesion of the composition. In certain embodiments, the composition further comprises a wax to improve chew smoothness and surface lubrication. The wax may comprise carnauba wax and may be present in an amount from about 1 percent to about 5 percent by weight of the total composition.

The composition may further include calcium carbonate to provide mild abrasive cleaning and mineral supplementation. Magnesium stearate may function as a lubricant during compression or forming. Glycerol may function as a plasticizer and humectant to maintain chew softness.

The composition may further include one or more high-intensity sweeteners selected from steviol glycosides, thaumatin, or combinations thereof. These sweeteners enhance sweetness without adding digestible sugars.

Vitamin E may be included as an antioxidant to preserve flavor stability and prevent oxidative degradation of natural components.

In certain embodiments, mastication releases polyphenolic compounds from the apple peel components. The mechanical disruption of the freeze-dried and fermented apple peel within the resilient gum matrix facilitates exposure and release of polyphenols into saliva during chewing.

The composition may further comprise natural apple flavor and natural peppermint flavor to enhance palatability.

In certain embodiments, the chewing gum composition is free of added mono- and disaccharides. As used herein, "free of added sugars" means that no sucrose, glucose, fructose, maltose, lactose, or other added mono- or disaccharides are intentionally incorporated into the formulation. Trace sugars inherently present in apple peel do not constitute added sugars.

In certain embodiments, calcium carbonate may be present from about 0.2 percent to about 3 percent by weight to provide mild abrasive cleaning and mineral supplementation. Magnesium stearate may be present from about 0.2 percent to about 3 percent by weight and may function as a lubricant during forming.

Optional humectants such as glycerol may be present from about 0.1 percent to about 2 percent by weight.

High intensity sweeteners may be present from about 0.01 percent to about 1 percent by weight. High intensity sweeteners include steviol glycosides derived from *Stevia rebaudiana* (e.g., stevioside, rebaudioside A, rebaudioside M), monk fruit extract (mogrosides), thaumatin, sucralose, acesulfame potassium, saccharin, neotame, advantame, and combinations thereof.

Antioxidants such as vitamin E May be present from About 0.01 percent to about 0.5 percent by weight.

What is claimed is:

1. A chewing gum composition comprising:
a chicle gum base;
a polyol sweetener comprising erythritol;
freeze-dried apple peel;
fermented dried apple peel; and
a dietary fiber system comprising (i) a resistant starch and (ii) a soluble acacia-derived fiber,
wherein the resistant starch is distinct from fiber naturally present in the apple peel components.

2. The chewing gum composition of claim 1, wherein the chewing gum composition comprises at least 35 percent by weight gum base and at least 20 percent by weight erythritol, the percentages being based on the total weight of the chewing gum composition.

3. The chewing gum composition of claim 1, wherein the resistant starch comprises a type 2 or type 4 resistant starch.

4. The chewing gum composition of claim 1, wherein the resistant starch comprises a chemically modified distarch.

5. The chewing gum composition of claim 1, wherein the resistant starch comprises at least 1 percent by weight of the total composition.

6. The chewing gum composition of claim 1, wherein the soluble acacia-derived fiber comprises at least 2 percent by weight of the total composition.

7. The chewing gum composition of claim 1, wherein the freeze-dried apple peel and fermented dried apple peel are present in substantially equal amounts.

8. The chewing gum composition of claim 1, wherein the combined freeze-dried apple peel and fermented dried apple peel comprise at least 3 percent by weight of the total composition.

9. The chewing gum composition of claim 1, further comprising acetylated distarch adipate.

10. The chewing gum composition of claim 1, further comprising a wax.

11. The chewing gum composition of claim 1, wherein the resistant starch comprises a type 2 and type 4 resistant starch.

12. The chewing gum composition of claim 2, wherein the resistant starch comprises a type 2 or type 4 resistant starch.

13. The chewing gum composition of claim 2, wherein the resistant starch comprises a chemically modified distarch.

14. The chewing gum composition of claim 2, wherein the resistant starch comprises at least 1 percent by weight of the total composition.

15. The chewing gum composition of claim 2, wherein the soluble acacia-derived fiber comprises at least 2 percent by weight of the total composition.

16. The chewing gum composition of claim 2, wherein the freeze-dried apple peel and fermented dried apple peel are present in substantially equal amounts.

17. The chewing gum composition of claim 2, wherein the combined freeze-dried apple peel and fermented dried apple peel comprise at least 3 percent by weight of the total composition.

18. The chewing gum composition of claim 2, further comprising acetylated distarch adipate.

19. The chewing gum composition of claim 2, further comprising a wax.

20. A chewing gum composition comprising:

a gum base comprising chicle;

a polyol sweetener comprising erythritol;

freeze-dried apple peel; and fermented dried apple peel.

* * * * *